United States Patent [19]

Poje et al.

[11] Patent Number: 5,168,593
[45] Date of Patent: Dec. 8, 1992

[54] TOOL FOR CLEANING ENDOSCOPES

[75] Inventors: Alan C. Poje, Concord; John M. Dombrosky, Euclid, both of Ohio

[73] Assignee: Mill-Rose Laboratories, Inc., Mentor, Ohio

[21] Appl. No.: 786,309

[22] Filed: Nov. 1, 1991

[51] Int. Cl.⁵ .............................................. B08B 9/02
[52] U.S. Cl. ................................. 15/104.2; 15/104.33; 15/164; 15/206; 401/289
[58] Field of Search ............. 15/104.33, 104.2, 104.16, 15/104, 165, 164, 206

[56] References Cited

U.S. PATENT DOCUMENTS

| | | | |
|---|---|---|---|
| 1,154,369 | 9/1915 | Browning | 15/104.33 |
| 1,421,529 | 7/1922 | Millhouse | 15/104.33 |
| 2,608,421 | 8/1952 | Schnepp | 15/104.33 |
| 2,739,585 | 3/1956 | Ayre | 15/104.33 |
| 3,283,353 | 11/1966 | Kirk | 15/104.33 |
| 5,003,657 | 4/1991 | Boiteau et al. | 15/104.33 |

OTHER PUBLICATIONS

Gastroenterology Nursing, vol. 12, No. 4, Spring 1990, p. 301.
Gastroenterology Nursing, vol. 13, No. 2, Fall 1990, p. 126.

*Primary Examiner*—Edward L. Roberts
*Attorney, Agent, or Firm*—Watts, Hoffmann, Fisher & Heinke

[57] ABSTRACT

A cleaning tool is disclosed for cleaning hard-to-reach and sharply curved passages, particularly those of endoscopes. The tool includes a brush connected to a spring. The spring is connected to a length of flexible tubing. A stiffening member is disposed within the flexible tubing. A fluid passage is provided within the tubing for delivering cleaning fluid or rinsing fluid to the interior of the object being cleaned.

18 Claims, 6 Drawing Sheets

TOOL FOR CLEANING ENDOSCOPES

BACKGROUND OF THE INVENTION

1. Field of the Invention

The present invention relates to flexible cleaning tools, and more particularly, to flexible brush tools for cleaning endoscopes including means for delivering fluid.

2. Description of Related Art

Colonoscopes, bronchoscopes and similar endoscopes require cleaning after each use. Endoscopes have long flexible tubes containing various passages. Some endoscope passages are for transmitting light beams to illuminate or observe the area being operated on. Other passages serve as suction channels or as operating tool passageways. The operating and suction passages must be cleaned after each use with a surgical cleaner and/or disinfectant. The passages are hard to reach since they are long and narrow, and in some places, sharply curved.

A reusable brush, small, but similar in construction to a conventional bottle brush, has been used for cleaning endoscopes; that is, a brush having a long and flexible teflon-coated wire stem, a handle at one end, and a group of bristles at the other end. In use, the brush is inserted into the endoscope passages and manipulated while the endoscope is immersed in cleaning fluid. This brush, while somewhat flexible, nevertheless lacks the ability to effectively negotiate sharp turns in the endoscope passages.

The trend in medical supplies is to make products disposable to eliminate cross-contamination. One disposable prior art cleaning tool employed a length of flexible plastic tubing having a small brush fitted into one end. Near the brush tip, a hole was formed in the tubing wall to permit fluid circulation. The plastic tubing tended to kink and bend when pushed in the process of cleaning which reduced its effectiveness. In addition, the brush lacked the ability to negotiate the sharp turns in the endoscope passages.

SUMMARY OF THE INVENTION

Basically, the tool comprises a cleaning member, a length of flexible plastic tubing, a spring, and a stiffening member. The spring is connected to the cleaning member and extends from the tubing. The stiffening member is disposed within and extends a substantial distance along the length of the tubing.

The stiffening member is sized smaller in cross section than the interior of the tubing to provide a fluid passage between the stiffening member and the tubing. The tool includes a fluid inlet and outlet communicating with the passage.

In one embodiment, the spring is connected to the end of the stiffening member. In another embodiment, the spring and the stiffening member form one piece.

BRIEF DESCRIPTION OF THE DRAWINGS

Preferred embodiments of the invention are shown in the accompanying drawings in which.

DESCRIPTION OF THE PREFERRED EMBODIMENTS

Figure 1:
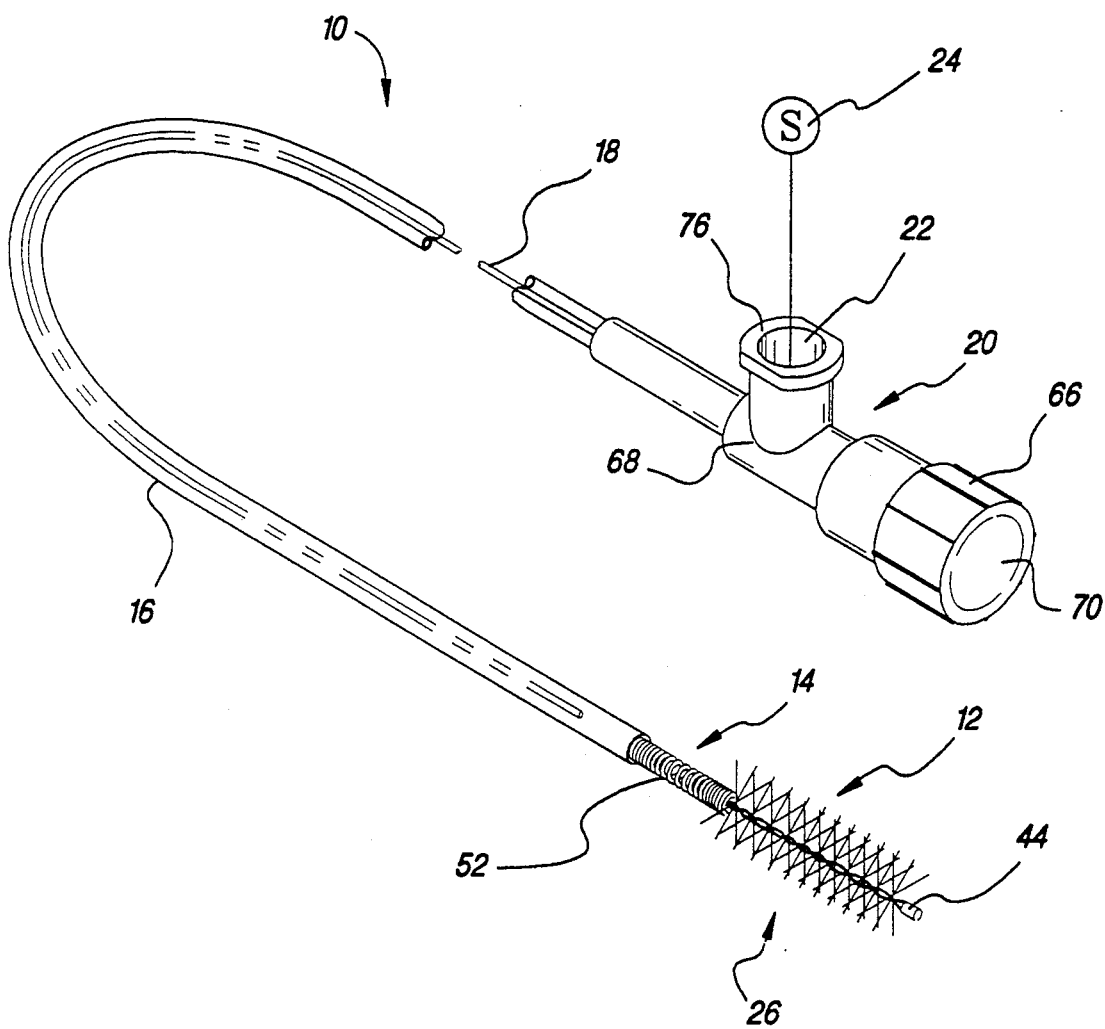
FIG. 1 is a perspective view of a tool constructed in accordance with the present invention.

Referring to FIG. 1, a disposable cleaning tool 10 embodying the present invention includes a cleaning member, a spring 12, a length of flexible plastic tubing 14, a stiffening member 16, and a fitting 18. The preferred cleaning member is a brush 20. The brush 20 is supported by the spring 12 which extends from the distal end of the tubing 14. In the preferred embodiment, the spring 12 is a coil spring. The stiffening member 16 is connected to the fitting 18 near the proximal end of the tool 10 and extends within and essentially along the full length of the tubing 14. In use, the tool 10 can be forced through a small diameter elongated passage to be cleaned, such as a passage 24 (FIG. 7) of an endoscope. The spring allows sharp bends in the passage 24 to be followed by the brush 20.

The tool 10 permits fluid to circulate inside the passage 24 being cleaned. Fluid may flow through the interior of the spring 12 which communicates with the interior of the tubing 14, and between the coils 13 of the spring. The fitting 18 has an opening communicating with the interior of the tubing 14. Advantageously, the fluid may be forced through the tubing 14 under pressure, as with a syringe 28, to exit through the spring for flushing endoscope passages.

Figure 3:
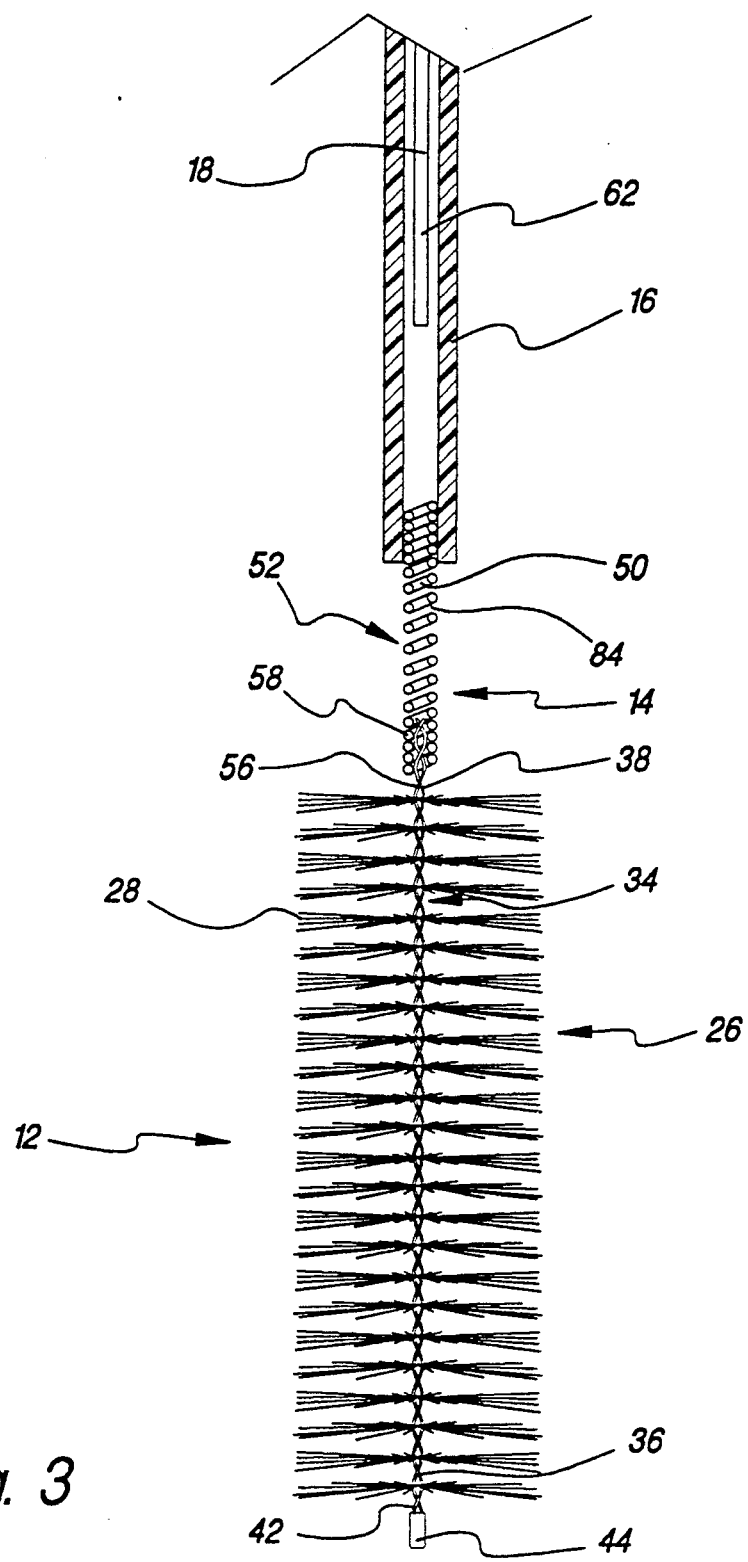
FIG. 3 is a view, partly in longitudinal section and partly in elevation, of the distal end of the tool of FIG. 1.

Referring to FIGS. 1 and 3, one preferred brush 20 has stiff nylon bristles 22 for effective scrubbing. The brush 20 is made from two twisted stainless steel wires 30. The bristles 22 are clamped tightly between a portion of the twisted wires 30. A portion of the twisted wires 30 extending beyond the bristles forms a stem 32 that is fitted tightly inside the distal end of the spring 12. Adhesive is preferably used to ensure a secure connection between the brush 20 and the spring 12; however, the stem 32 may simply be securely force-fitted into the distal end of the spring 12. A cap 34 is secured to the tip of the brush 20. The cap 34 serves to blunt the tip of the brush 20 to avoid scratching the endoscope or catching the tip during cleaning. The brush diameter is variable as determined by the size of the passages 22 being cleaned; however, one preferred brush diameter is 6 mm.

Figure 7:
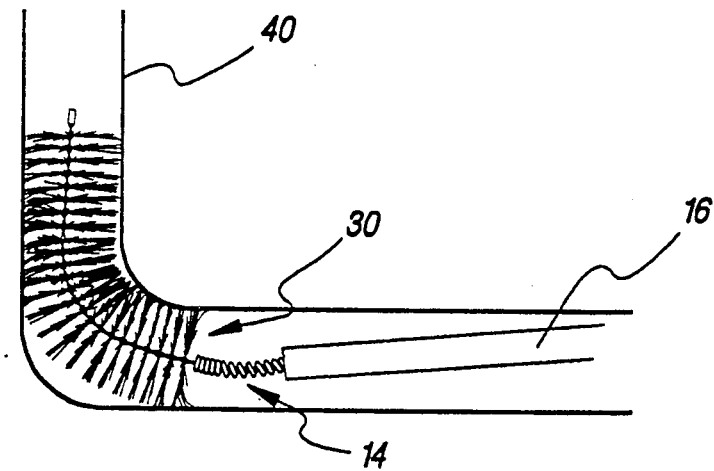
FIG. 7 is a diagrammatic view of the tool of FIG. 3 inside a passage.

The brush 20 shown in FIGS. 1 and 3 is of such a length (approximately ⅝" inch) that it must flex in order to negotiate sharp turns in typically-sized endoscope passages as illustrated diagrammatically in FIG. 7. Very thin, flexible wires 30 are used to make the brush 20 resulting in a brush that has spring-like characteristics.

The spring 12 serves to form a highly flexible connection between the tubing 14 and the brush 20. Referring to FIG. 3, the spring 12 is preferably a cylindrical, stainless steel, coil spring 12 having a hollow interior. The distal end of the spring is connected to the brush stem 32 and the proximal end fits within and is connected to the distal end of the tubing 14. The twisted wires of the brush stem 32 form thread-like grooves 36 in the stem 32. These "threads" 36 interengage with the coils of the spring 12 to form a mechanical connection. The spring 12 is bonded with adhesive to the tubing 14 ensure that the spring 12 does not separate from the tubing 14. The outer diameter of the spring 12 is approximately the same as the inner diameter of the flexible tubing 14, which in the preferred and illustrated embodiment, is approximately 0.040 inch. The inner diameter of the spring is approximately 0.020 inch. The coils 13 of an intermediate portion of the spring are preferably spaced, as shown in FIG. 1.

The flexible tubing 14 forms the body of the tool 10 and serves to conduct fluid. The length of the tubing 14 is variable depending on the application. For example, the preferred total length of a tool 10 for gastrointestinal scopes is 240 cm. The total preferred length of a tool 10 for cleaning bronchoscopes is 115 cm. The preferred tubing material is polypropylene. The preferred and illustrated tubing 14 has an inner diameter of 0.040 inch and an outer diameter of 0.070 inch.

The stiffening member 16 is disposed inside the flexible tubing 14 and serves to resist bending and kinking of the tubing 14. The member 16 extends substantially the length of the tubing 14, though not as far as the spring 12 in the distal direction as seen in FIG. 3. The member 16 is secured to the fitting 18, which is secured to the flexible tubing 14. Preferably, the stiffening member 16 is a stainless steel wire approximately 0.018 inch in diameter.

Figure 2:
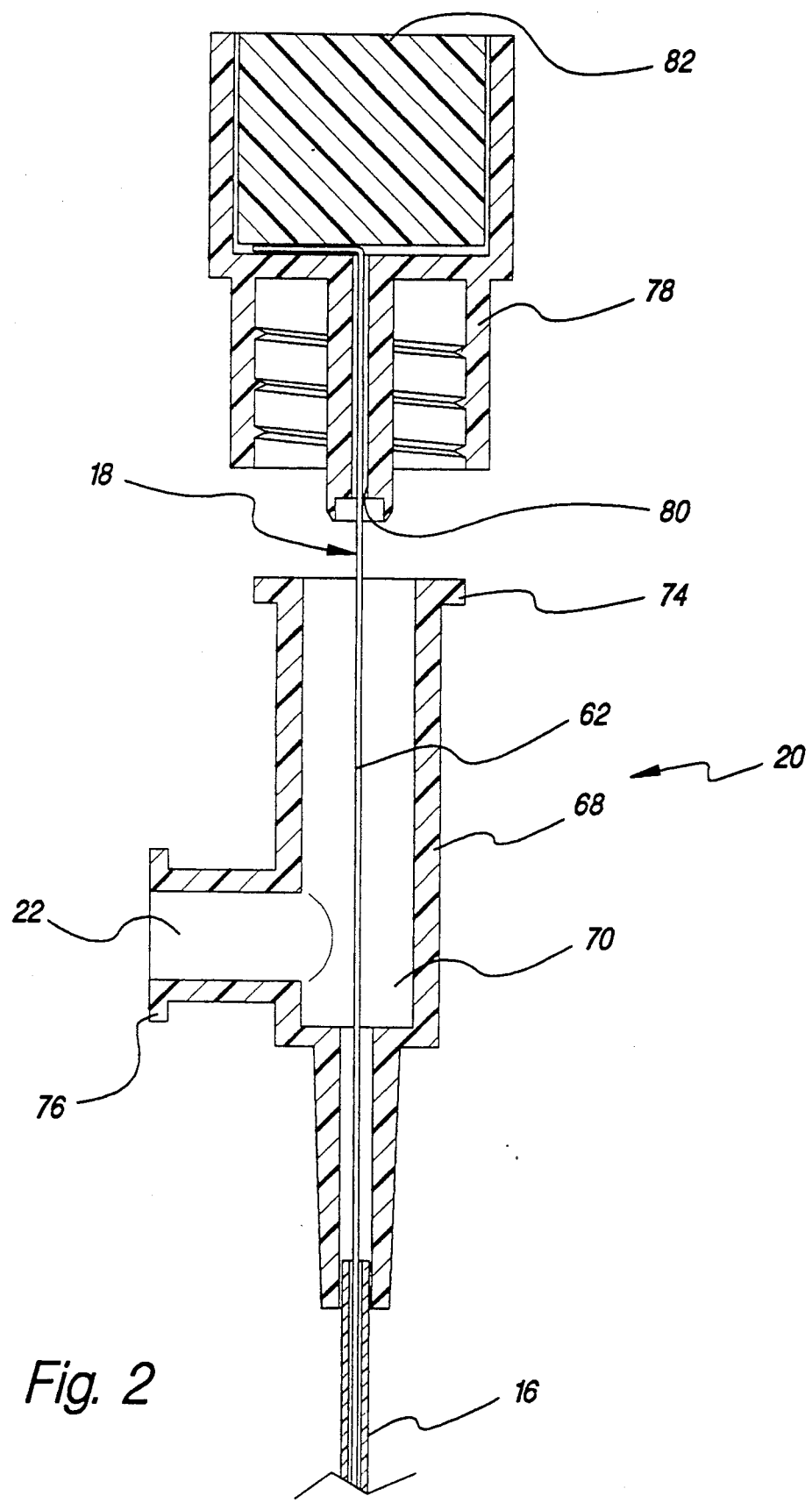
FIG. 2 is a view, partly in longitudinal section and partly in elevation, of the proximal end of the tool of FIG. 1 partially disassembled.

Referring to FIG. 2, the fitting 18 is located at the proximal end of the tool 10 and serves to join the tubing 14 to the stiffening member 16. The fitting 18 provides the opening 26 for fluid to enter the tubing 14. The preferred and illustrated fitting is a "T" luer adaptor fitting 18. The fitting 18 includes a central cavity 38 communicating with the interior of the flexible tubing 14. Two Female luer connectors 40, 42 are formed on the fitting 18 to communicate with the cavity 38. The first connector 40 is in axial alignment with the cavity 38 and the second 42 is normal thereto. The axially aligned luer connector 40 is sealed with a threaded cap 44. The cap 44 includes a small central passage 46 through which the stiffening member 16 extends and terminates in a portion 17 bent approximately 90°. A plug 48 is placed in the cap 44 to secure the member 16 to the cap 44 and to seal the cap 44. Finally, the cap 44 is threaded onto the luer connector 40 to secure the stiffening member 16 and the cap 44 to the fitting 18.

The second luer connector 42 may be used to introduce fluids such as cleaning fluid, disinfectant, or rinsing fluid into the interior of the tubing 14. The syringe 28 or other pump outlet may be connected to the luer fitting 42. When the syringe 28 is operated, fluid will flow through the cavity 38 and the flexible tubing 14. After exiting the tubing 14, the fluid enters the interior of the spring 12. The fluid exits the spring 12 between its coils.

Figure 4:
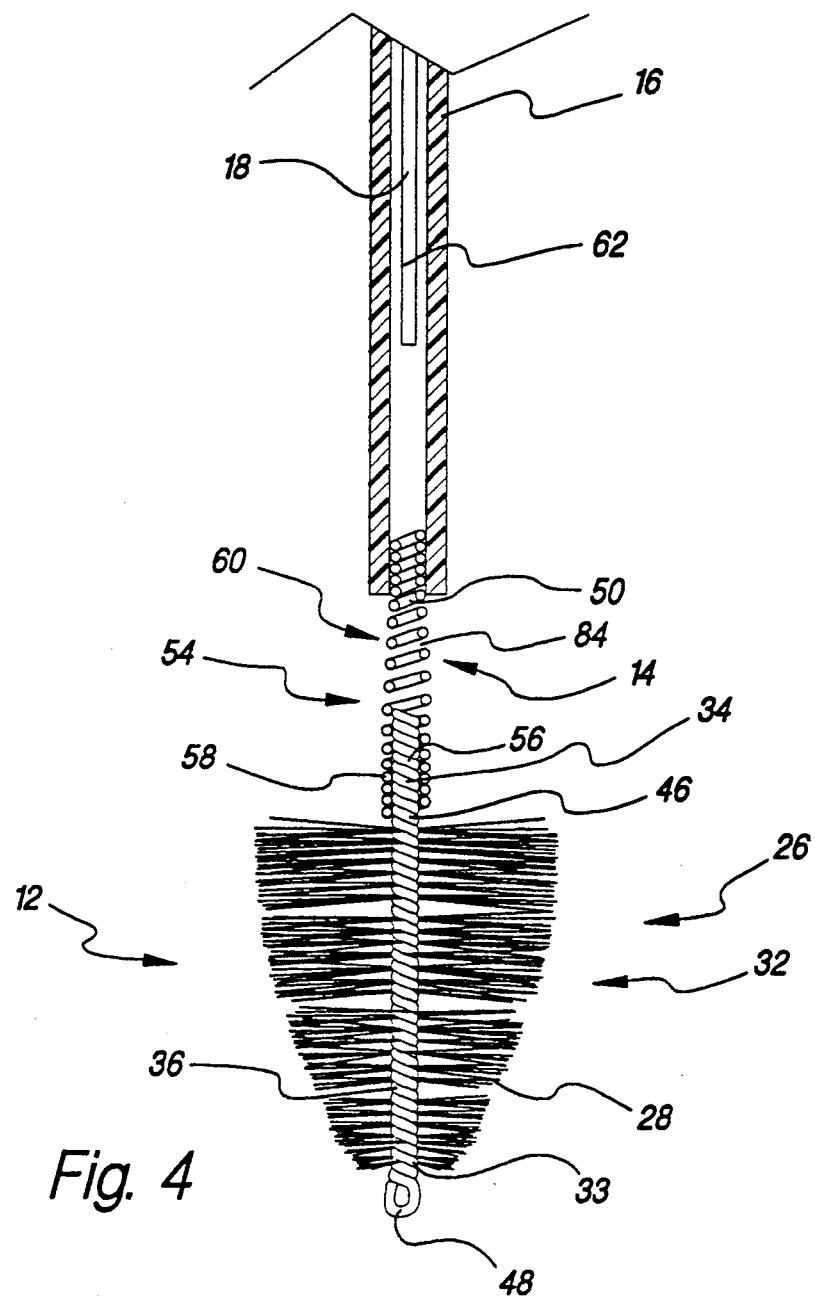
FIG. 4 is a view, partly in longitudinal section and partly in elevation, of the distal end of another embodiment of the tool.
Figure 8:
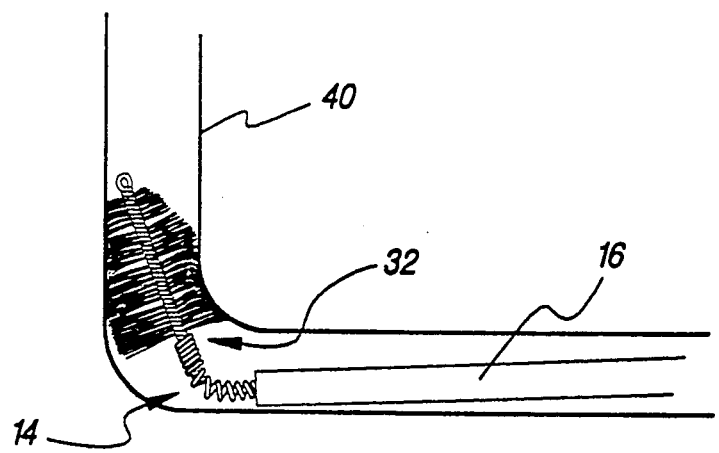
FIG. 8 is a diagrammatic view of the tool of FIG. 4 inside a passage.

A tool 50 of a second embodiment, shown in FIG. 4, differs from the tool 10 of FIGS. 1 and 3 only in the construction of its brush and spring. This tool 50 relies on the articulation provided by a spring 52 to negotiate turns as shown in FIG. 8. A brush 54, like the brush of FIG. 3, is made from two twisted stainless steel wires 56. The brush 54 has a relatively short length as compared to that of the embodiment of FIG. 3. Unlike the brush 20 shown in FIG. 3, the brush 54 is made of relatively sturdy twisted stainless steel wires 56 and is not readily flexible. Like the brush of FIG. 3, stiff nylon bristles 58 are clamped between a portion of the twisted wires 56, and a portion of the wires beyond the bristles forms a stem 60. This brush 54, because it is relatively short, is able to negotiate turns in the passage 24 without flexing, as shown diagrammatically in FIG. 8. The brush 54 has a blunt tip formed by a loop 62 of the wire 56.

Referring to FIG. 4, the spring 52 has a tapered portion 64 where the inner and outer diameters of the spring 52 increase in the distal direction. The larger distal end of the spring 52 accommodates the relatively thick stem 60 and the smaller proximal end fits into, and is bonded to, the distal end of a length of tubing 66 in which a stiffening member 68 is located. The distal end of the tapered spring 52 has an outer diameter of approximately 0.053 inch and an inner diameter of approximately 0.030 inch. The dimensions of the proximal end of the tapered spring 52 are approximately the same as those given above for the cylindrical spring 12 of the embodiment of FIG. 3.

Figure 5:
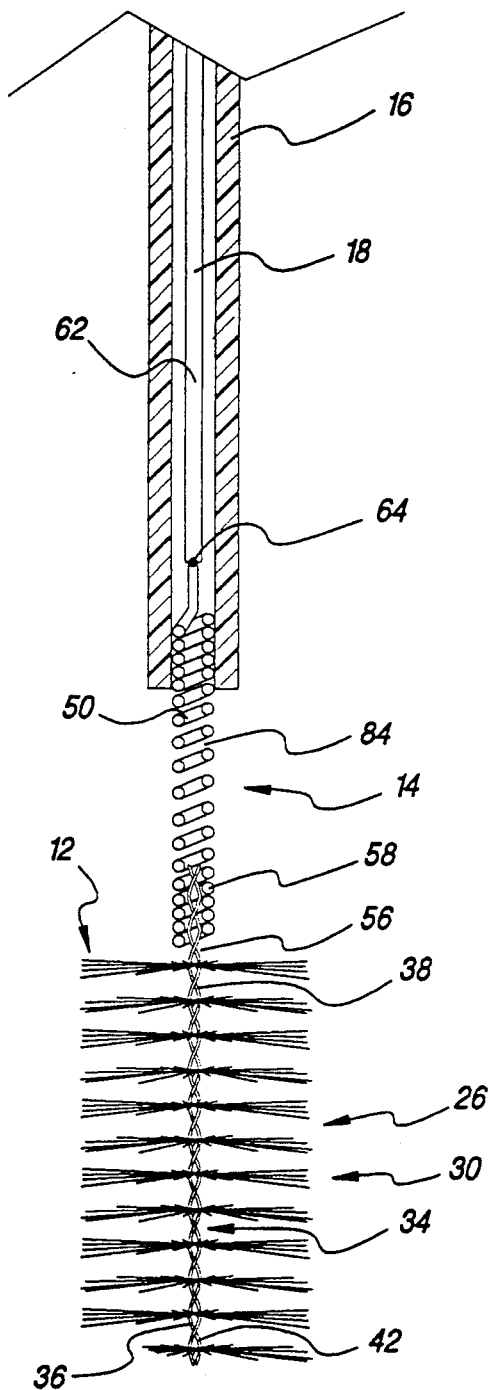
FIG. 5 is a view, partly in longitudinal section and partly in elevation, of the distal end of another embodiment of the tool.

A tool 70 of a third embodiment, as shown in FIG. 5, differs from the embodiment of FIGS. 1 and 3 only in the construction of the spring and the stiffening member. Here, a spring 72 is connected to a stiffening member 74 with a butt weld 76. A brush 78 is connected to the spring 72 in the same manner as the embodiment of FIG. 3. The spring 72 is fitted into the distal end of a length of flexible tubing 80 as in the embodiment of FIG. 3. The proximal end of the stiffening member 74 is connected to a fitting as in the embodiment of FIG. 2.

Figure 6:
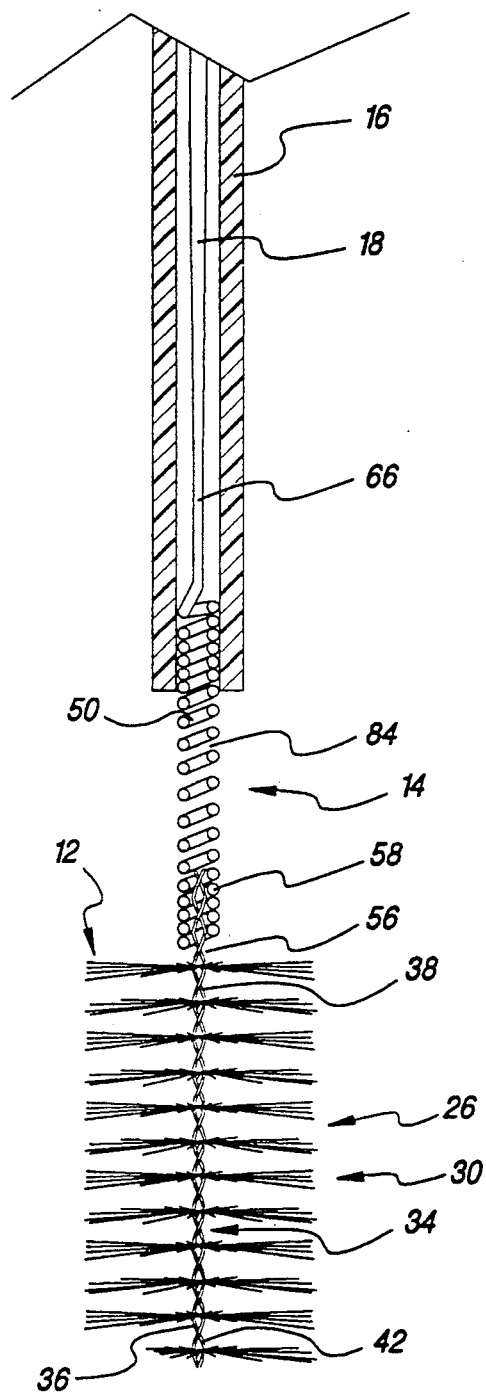
FIG. 6 is a view, partly in longitudinal section and partly in elevation, of the distal end of another embodiment of the tool.

A tool 82 of a fourth embodiment, as shown in FIG. 6, differs from the tool 10 of FIGS. 1 and 3 only in the construction of the spring and stiffening member. The tool 82 comprises a single part 84 forming a stiffening member and a spring. A brush 86 is connected to the part 84 in the same manner as the brush 20 is connected to the spring 12 in FIG. 3. The part 84 is fitted into the distal end of a length of tubing 88 as in the embodiment of FIG. 3. The proximal end of the part 84 is connected to a fitting in the same manner as shown in FIG. 2.

While preferred embodiments of this invention have been described in detail, it will be apparent that certain modifications or alterations can be made without departing from the spirit and scope of the invention set forth in the appended claims.

We claim:

1. A tool for cleaning passages of endoscopes or the like comprising:
   a cleaning member;
   a length of flexible plastic tubing;
   a spring connected to the cleaning member and extending from the tubing;
   a stiffening member disposed within and extending a substantial distance along the length of the tubing.

2. The tool of claim 1 wherein the stiffening member is sized smaller in cross section than the interior of the tubing to provide a fluid passage between the stiffening member and the tubing and wherein the tool includes a fluid inlet and outlet communicating with the passage.

3. The tool of claim 2 wherein the stiffening member extends essentially the full length of the tubing.

4. The tool of claim 3 wherein the stiffening member is connected to the tubing.

5. The tool of claim 3 wherein the stiffening member is secured to the spring.

6. The tool of claim 3 wherein the stiffening member and the spring form one piece.

7. The tool of claim 3 wherein the stiffening member is a wire.

8. The tool of claim 3 wherein the cleaning member is a brush.

9. The tool of claim 8 wherein the brush has nylon bristles.

10. The tool of claim 8 wherein the brush includes a stem coupled to the spring.

11. The tool of claim 2 wherein the spring is a coil spring having a hollow interior communicating with the fluid passage.

12. The tool of claim 8 wherein the cleaning member includes a stem formed by twisted wires, and wherein the twisted wires engage with coils of the coil spring to form a mechanical connection.

13. The tool of claim 11 wherein adjacent coils of the spring are spaced longitudinally.

14. The tool of claim 11 wherein the coil spring has an axially tapered portion in which the diameter of the interior passage and the outside diameter of the spring increases in a distal direction.

15. The tool of claim 1 wherein a luer-type fitting is joined to a proximal end of the tubing.

16. The tool of claim 15 wherein the stiffening member is connected to the luer-type fitting.

17. A tool for cleaning endoscopes or the like comprising:
    an elongated flexible plastic tube having a fluid inlet opening adjacent a proximal end and an outlet opening adjacent a distal end;
    a stainless steel coil spring connected to and extending from a distal end of the tube;
    a cleaning member having a stem connected to a distal end of the spring; and
    a stiffening member disposed within the tube and extending substantially the length thereof, the stiffening member being sized smaller in cross section than the interior of the tube to provide a fluid passage between the stiffening member and the tube;
    whereby fluid entering adjacent the proximal end and exiting adjacent the distal end of the tube enters the interior of the coil spring and exits the coil spring adjacent the cleaning member through spaces between the spring coils.

18. The tool of claim 17 wherein the cleaning member is a brush.

* * * * *